US00PP22865P3

(12) United States Plant Patent
Buhrow

(10) Patent No.: US PP22,865 P3
(45) Date of Patent: Jul. 17, 2012

(54) ***PENSTEMON* PLANT NAMED 'RED HEADED BEAUTY'**

(50) Latin Name: *Penstemon (palmeri×parryi)×superbus*
Varietal Denomination: Red Headed Beauty

(76) Inventor: Russ Buhrow, Tucson, AZ (US)

( * ) Notice: Subject to any disclaimer, the term of this patent is extended or adjusted under 35 U.S.C. 154(b) by 0 days.

(21) Appl. No.: 12/927,402

(22) Filed: Nov. 15, 2010

(65) Prior Publication Data

US 2012/0124709 P1 May 17, 2012

(51) Int. Cl.
*A01H 5/00* (2006.01)

(52) U.S. Cl. ..... Plt./465

(58) Field of Classification Search ..... Plt./465
See application file for complete search history.

*Primary Examiner* — Susan McCormick Ewoldt

(57) ABSTRACT

A new and distinct *Penstemon* hybrid named 'Red Headed Beauty' is characterized by: large, vivid purplish red to deep purplish red flowers with a slight scent appearing upon verticillate, subsecund thyrses with nodding tips; glabrous, glaucous, leathery, entire to obscurely toothed lance ovate leaves; large, windfirm plants with numerous flowering stalks. The plants have excellent vigor and longevity.

23 Drawing Sheets

Latin name: *Penstemon* (*palmeri*×*parryi*)×*superbus*.
Varietal denomination: 'Red Headed Beauty'.

BACKGROUND OF THE INVENTION

*Penstemon* is a large genus of the expanded plant family Plantaginaceae (formerly Scrophulariaceae) native to most of North America south to Guatemala. Many species, varieties and cultivars have been named and described. *Penstemons* are grown as flowering ornamentals.

The present invention relates to a new and distinct cultivar of *Penstemon* hybrid named 'Red Headed Beauty'. The cultivar originated in an open pollinated group of seedling offspring from a natural hybrid between *Penstemon palmeri* and *P. parryi* growing in a cultivated area near Tucson, Ariz. The new plant was selected by Russ Buhrow, a citizen of the United States of America residing in Tucson, Ariz., from the seedlings of a *Penstemon* interspecies hybrid. This hybrid is believed to have been crossed as an F1 hybrid with pollen of *Penstemon superbus*, resulting in several plants believed to be (*Penstemon palmeri*×*parryi*)×*superbus*. To the inventor's knowledge, this is the first report of the occurrence of this hybrid. One of the offspring proved to be particularly vigorous and had exceptional color and is the object of this application.

SUMMARY OF THE INVENTION

Among the features that distinguish the new *Penstemon* cultivar from all other available and commercial varieties of *Penstemon* known to the inventor are the following combination of characteristics: large, vivid purplish red to deep purplish red flowers with a slight scent appearing on verticillate, subsecund thyrses with nodding tips; glabrous, glaucous, leathery, entire to obscurely toothed lance ovate cauline leaves; large wind firm plants with numerous flowering stalks (5 to 30 on two year old plants). The plants exhibit excellent vigor and longevity.

'Red Headed Beauty' will be used as a perennial flowering ornamental, accent plant, for mass plantings and possibly, due to the long flower spikes, as a cut flower.

'Red Headed Beauty' is being propagated by a custom propagator. The propagation procedure is as follows:

Cuttings are prepared from the flowering stalks containing one or two nodes. The two node cuttings root faster and more reliably. Cuts are pretreated by wetting in Dip & Grow™ at a dilution of 1:10. The leaves of the lower node are removed from two node cuttings and cuttings are planted with the upper leaves above the media (Jiffy Performa™). Cuttings in liner flats are placed into a mist greenhouse without bottom heat with max/min temperatures of 90/65 F. Rooting is complete within 3 weeks.

The foregoing characteristics and distinctions come true to form and are established and transmitted throughout succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate specimens of the new cultivar displaying materials from the original selection of 'Red Headed Beauty' as well as propagated specimens growing near Tucson, Ariz. and Sahuarita, Ariz. depicted in color as nearly correct as it is possible to make in a color illustration of the character.

DETAILED PLANT DESCRIPTION

Figure 1:
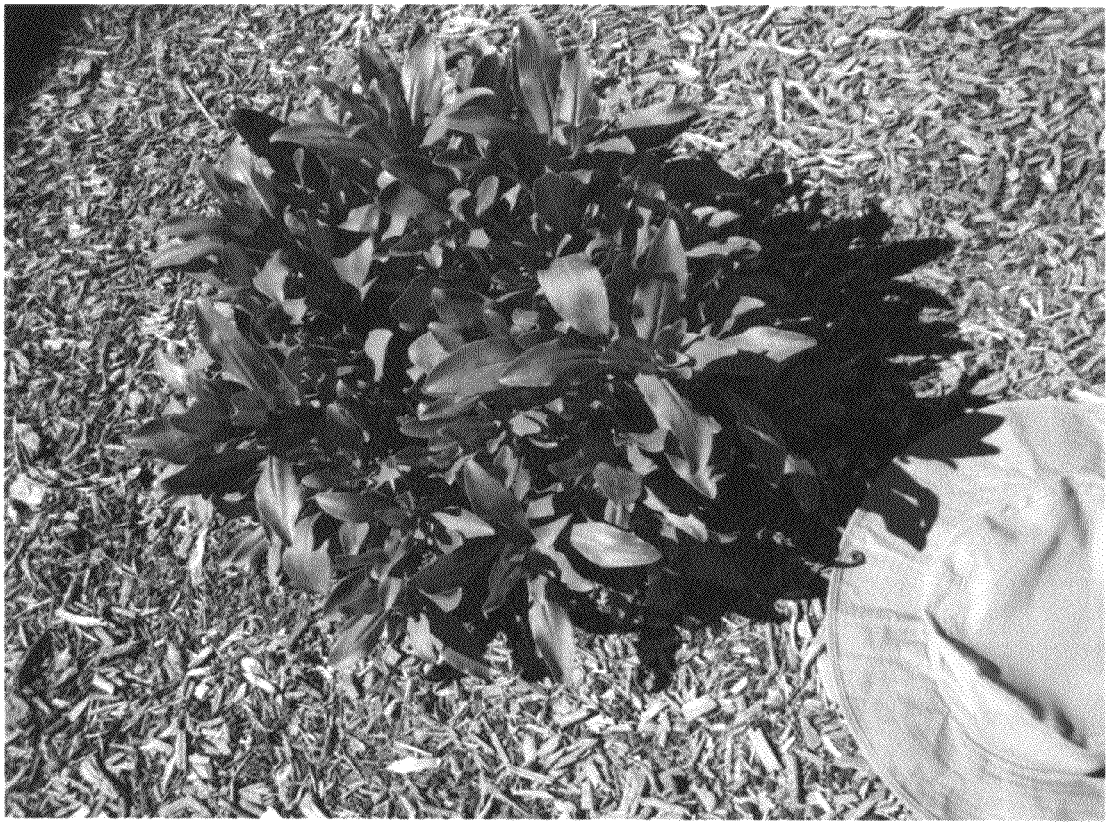
FIG. 1 shows a propagated specimen of 'Red Headed Beauty' growing vegetatively at Sahuarita, Ariz., taken Mar. 3, 2010.
Figure 2:
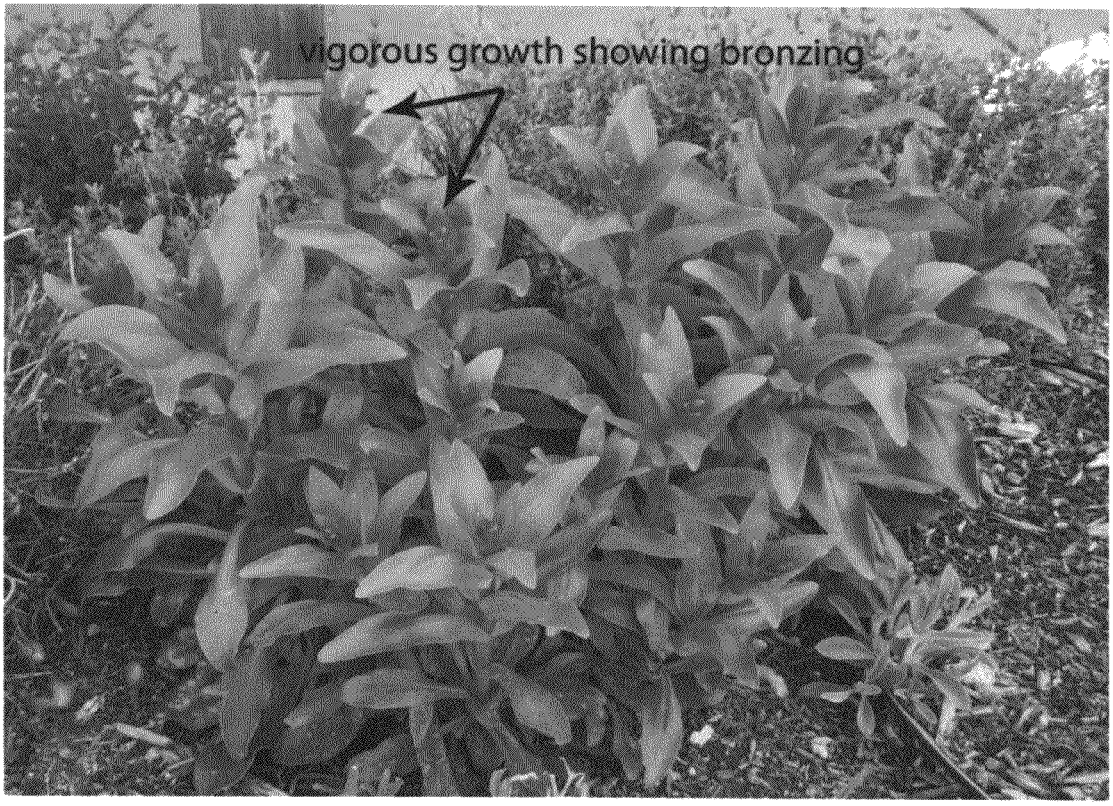
FIG. 2 shows a propagated stock plant specimen of 'Red Headed Beauty' in early flowering growth exhibiting temporary bronzing of the fast growing portions of the plant growing near Tucson, Ariz.
Figure 3:
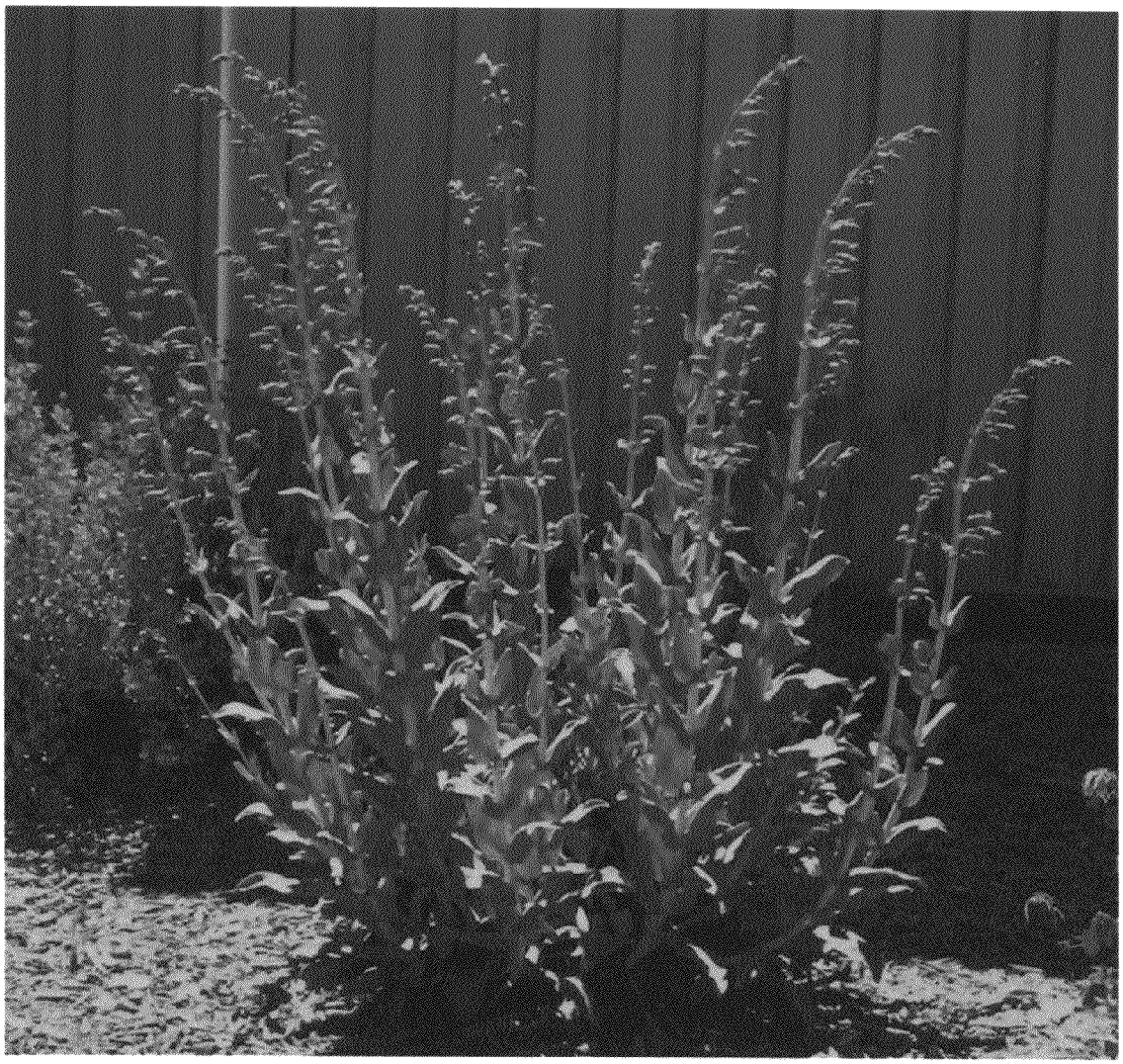
FIG. 3 shows the plant illustrated in FIG. 1 in early bloom, photo taken Apr. 1, 2010.
Figure 4:
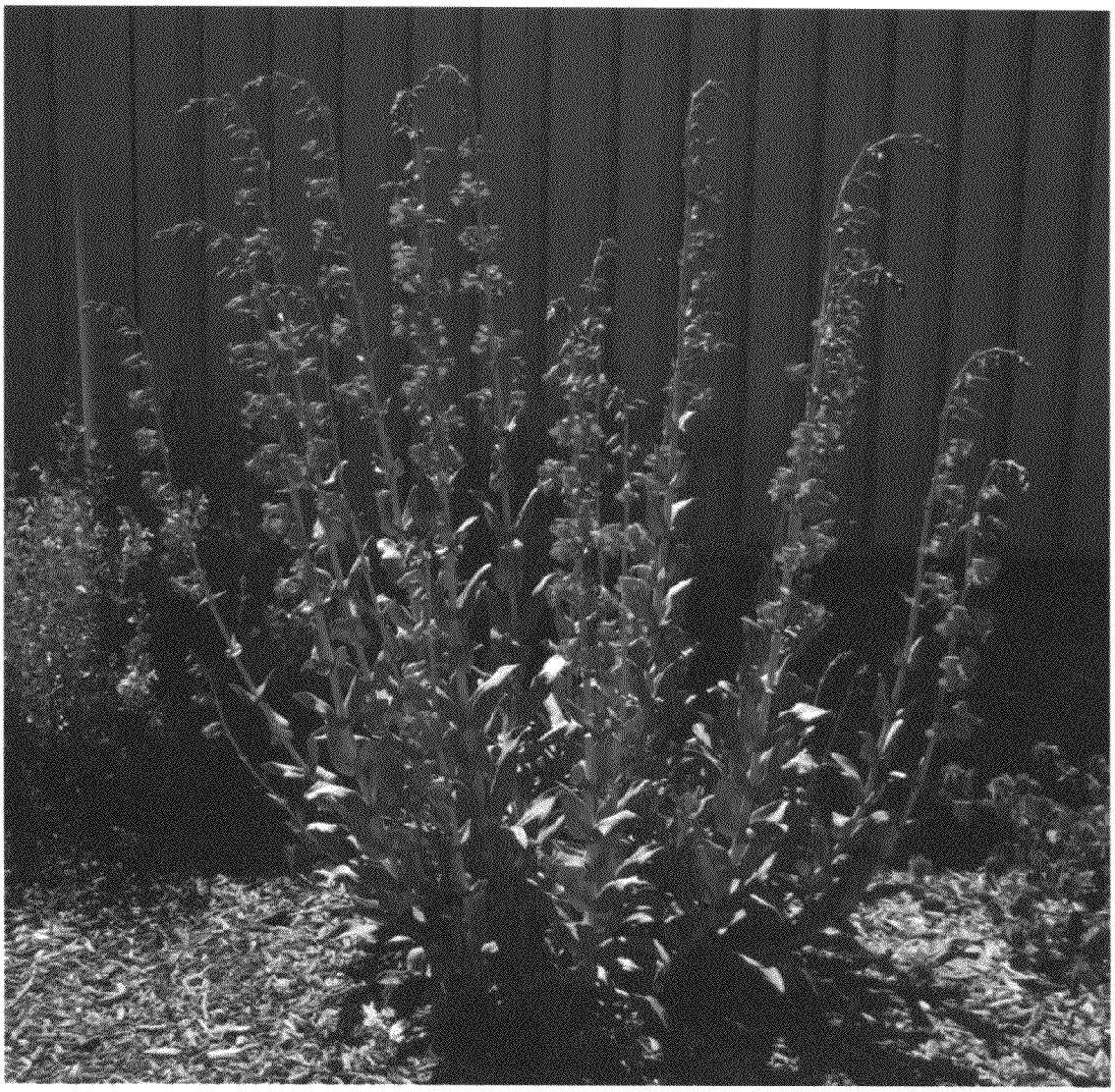
FIG. 4 shows the plant shown in FIG. 1 in full bloom, photo taken Apr. 14, 2010. Note the curved inflorescence tips distinctive to this variety.
Figure 5:
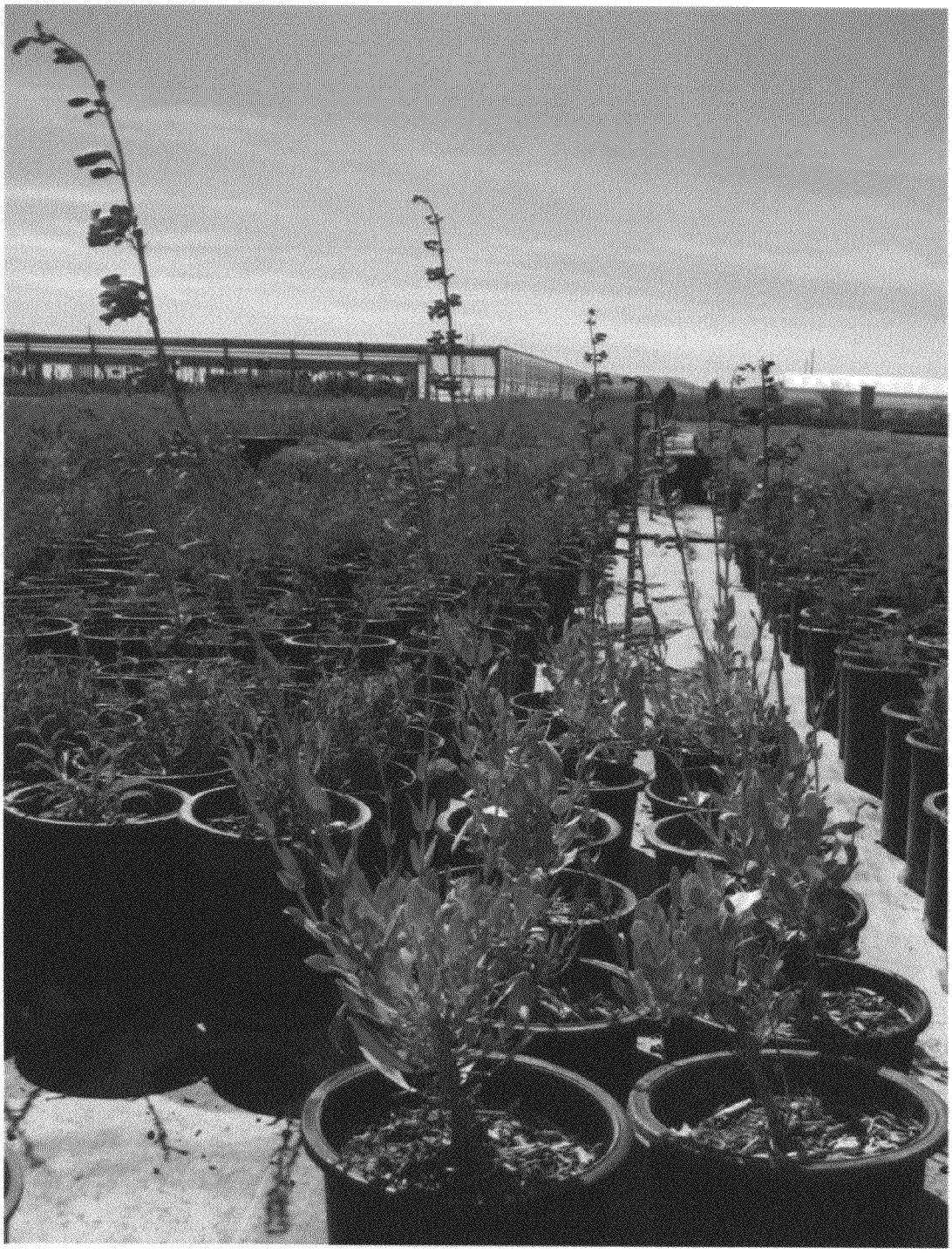
FIG. 5 shows thirteen propagated 'Red Headed Beauty' plants growing in five gallon pots (lower right) at Sahuarita, Ariz. under like conditions of low fertility and water, demonstrating that the plants are true to form and uniform. Photo was taken Apr. 14, 2010.
Figure 6:
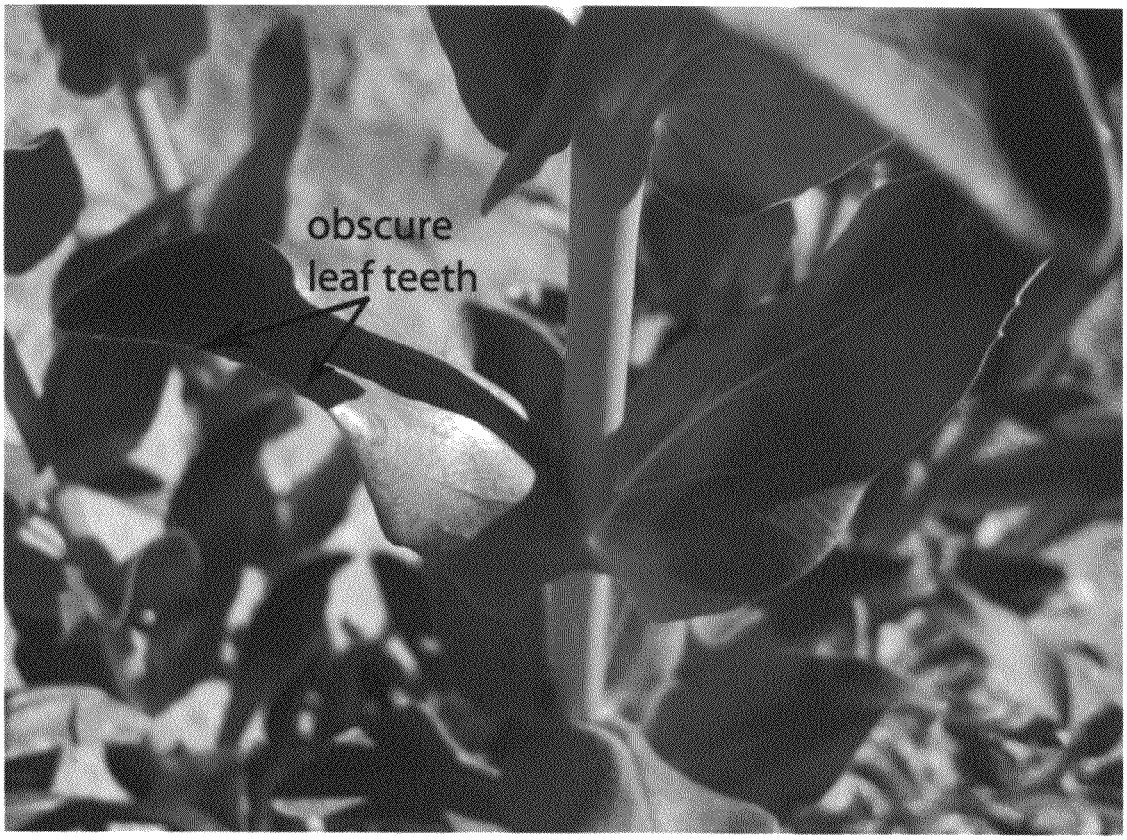
FIG. 6 shows the largest cauline leaves of the original 'Red Headed Beauty' plant growing in a cultivated area near Tucson, Ariz., photo taken Apr. 7, 2010.
Figure 7:
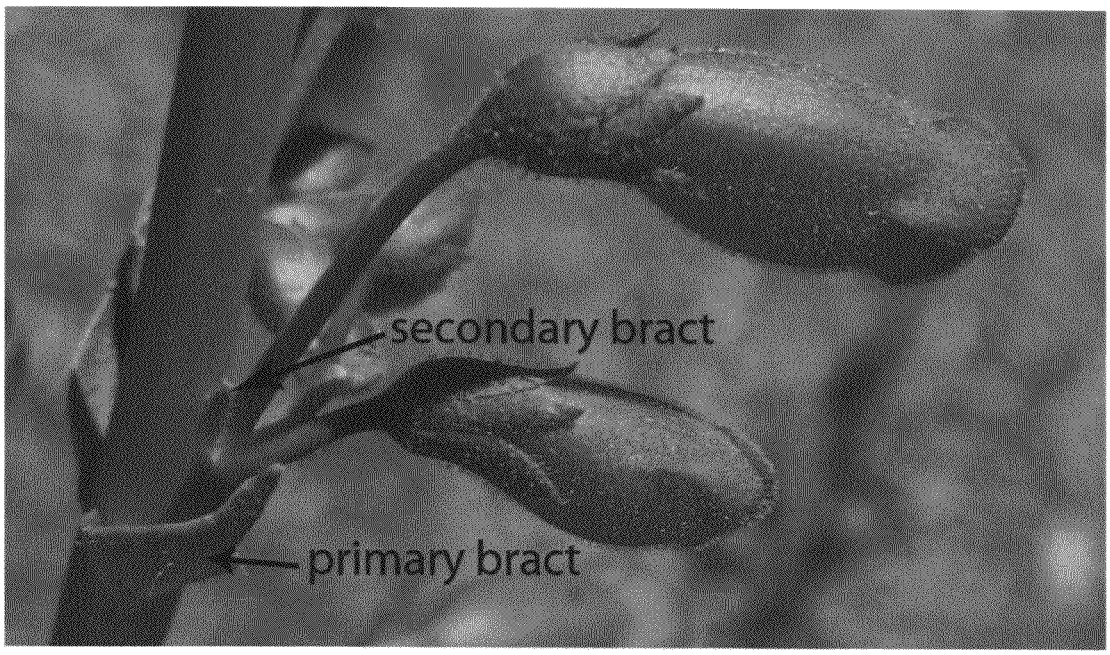
FIG. 7 illustrates developing flower buds and floral bracts of 'Red Headed Beauty' from the upper middle portion of an inflorescence from a the original plant growing near Tucson, Ariz., taken Apr. 14, 2010.
Figure 8:
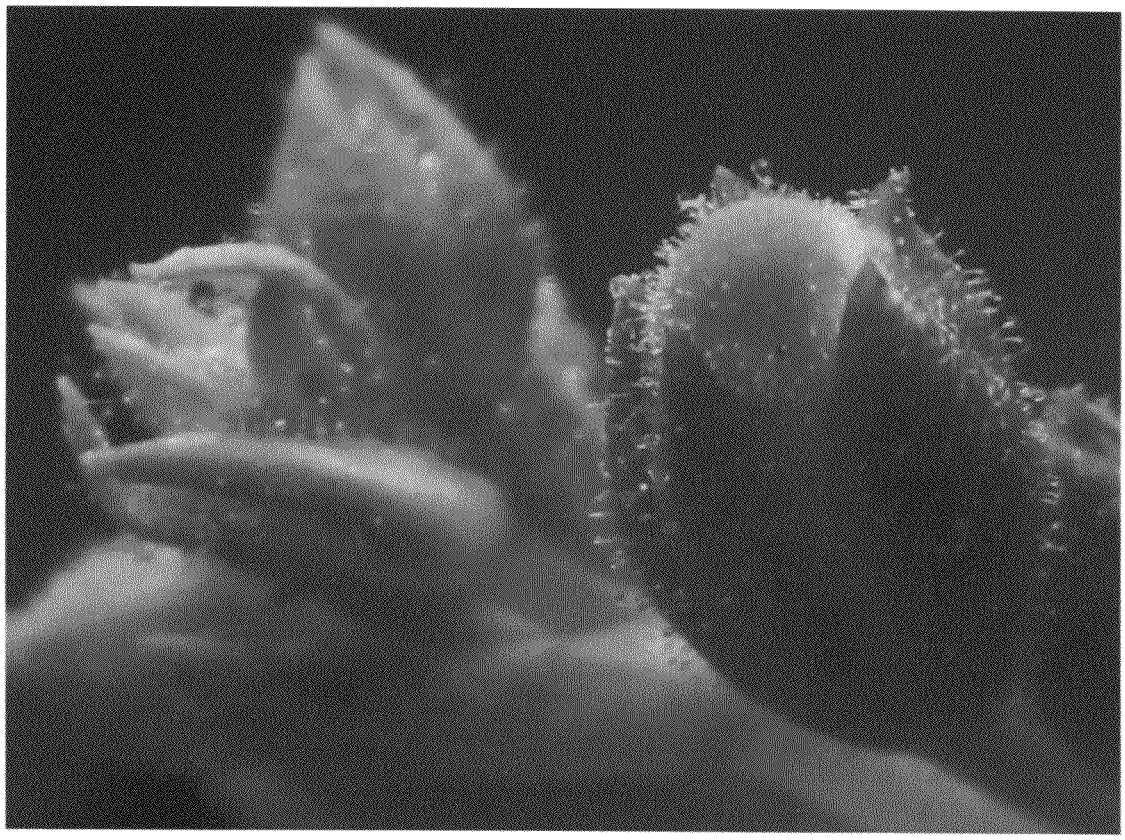
FIG. 8 is a macrophotograph of the terminal portion of an inflorescence of the 'Red Headed Beauty' original plant growing near Tucson, Ariz. showing developing bracts and flower buds, taken May 2, 2010.
Figure 9:
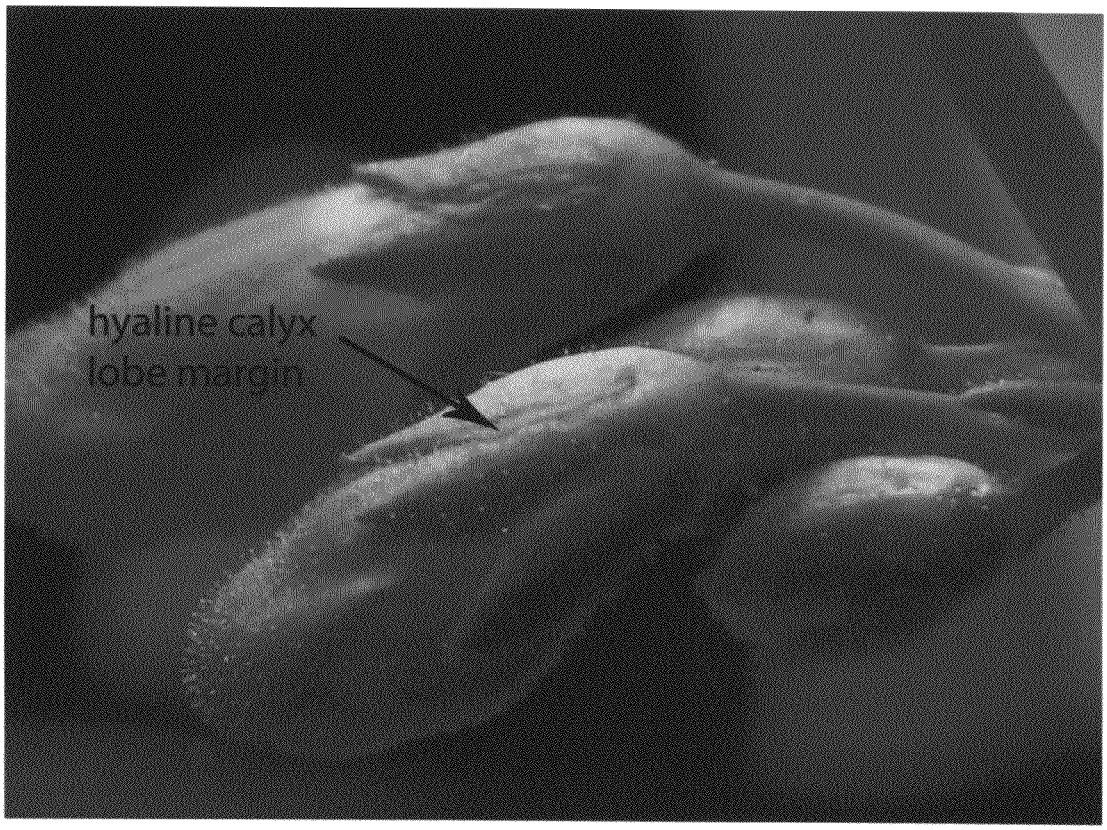
FIG. 9 is a macrophotograph of a bud cluster of the original 'Red Headed Beauty' plant growing near Tucson, Ariz. illustrating calyx details and showing the hyaline calyx lobe margins typical of this variety, taken May 2, 2010.
Figure 10:
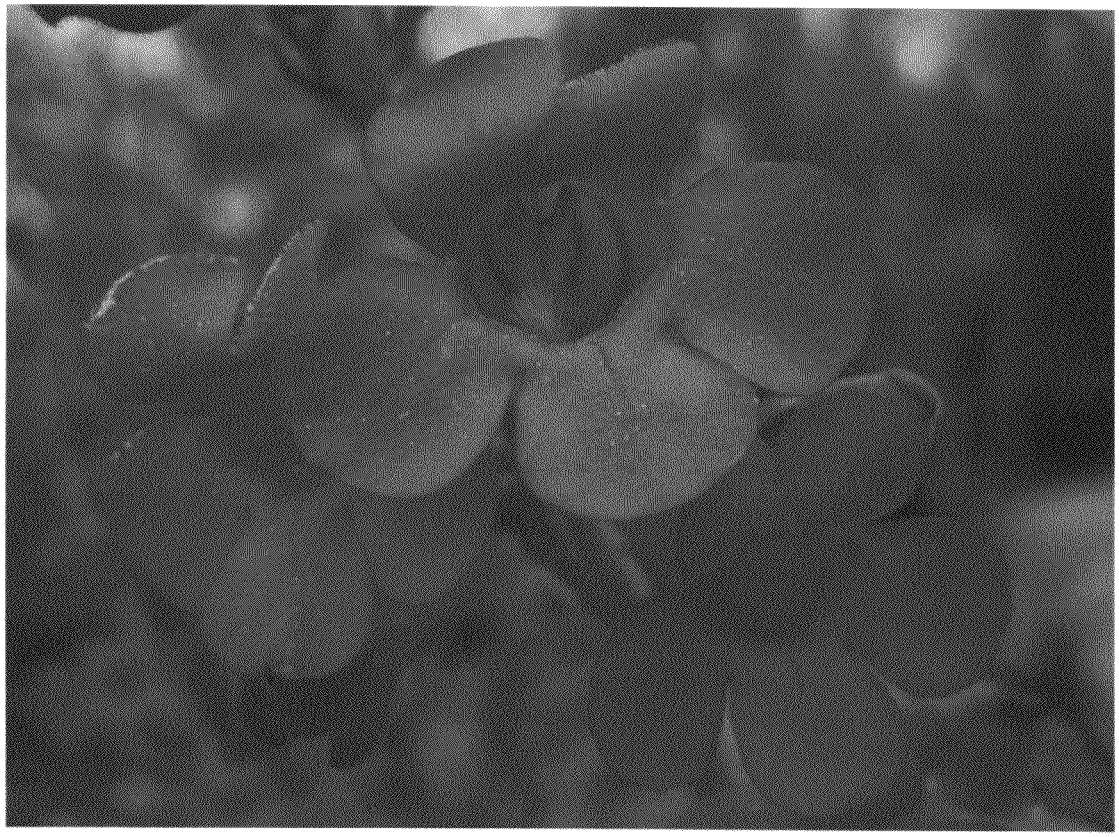
FIG. 10 is a closeup of a flower cluster of the original 'Red Headed Beauty' plant growing near Tucson, Ariz. Photo was taken Apr. 16, 2010.
Figure 11:
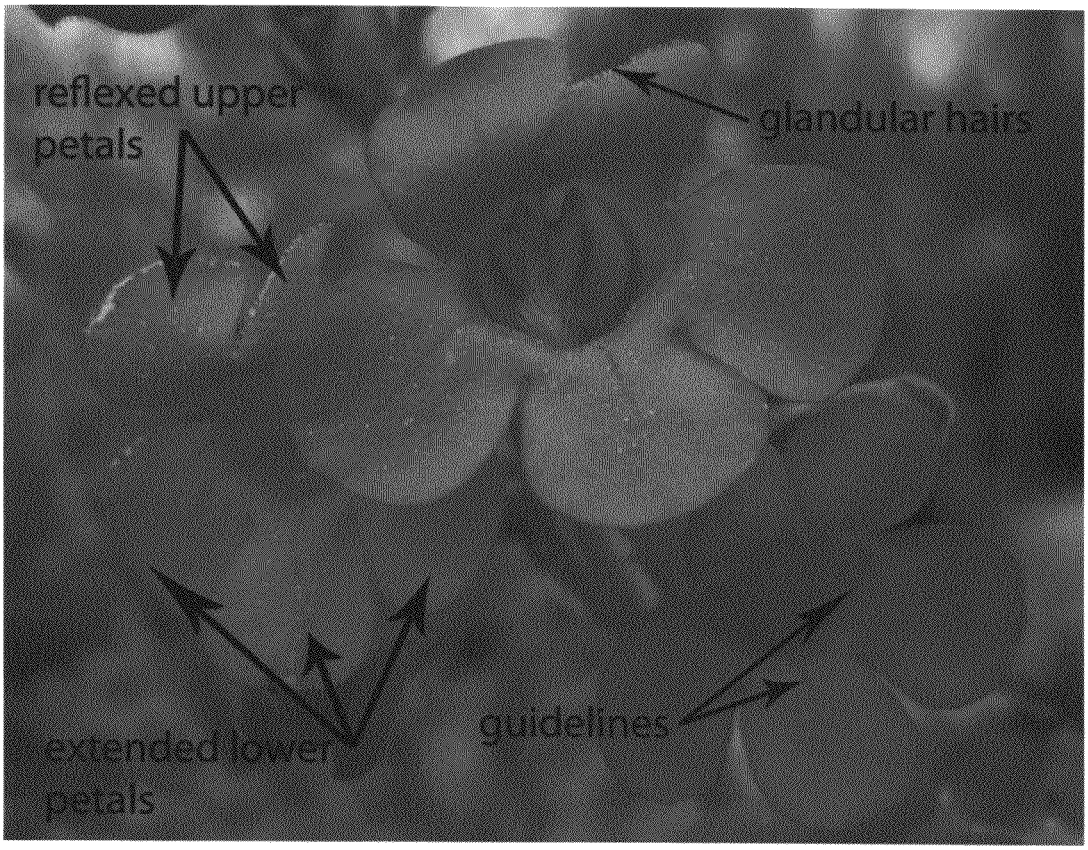
FIG. 11 is the same photograph as FIG. 10, but highlighting characteristics typical and unique to 'Red Headed Beauty'.
Figure 12:
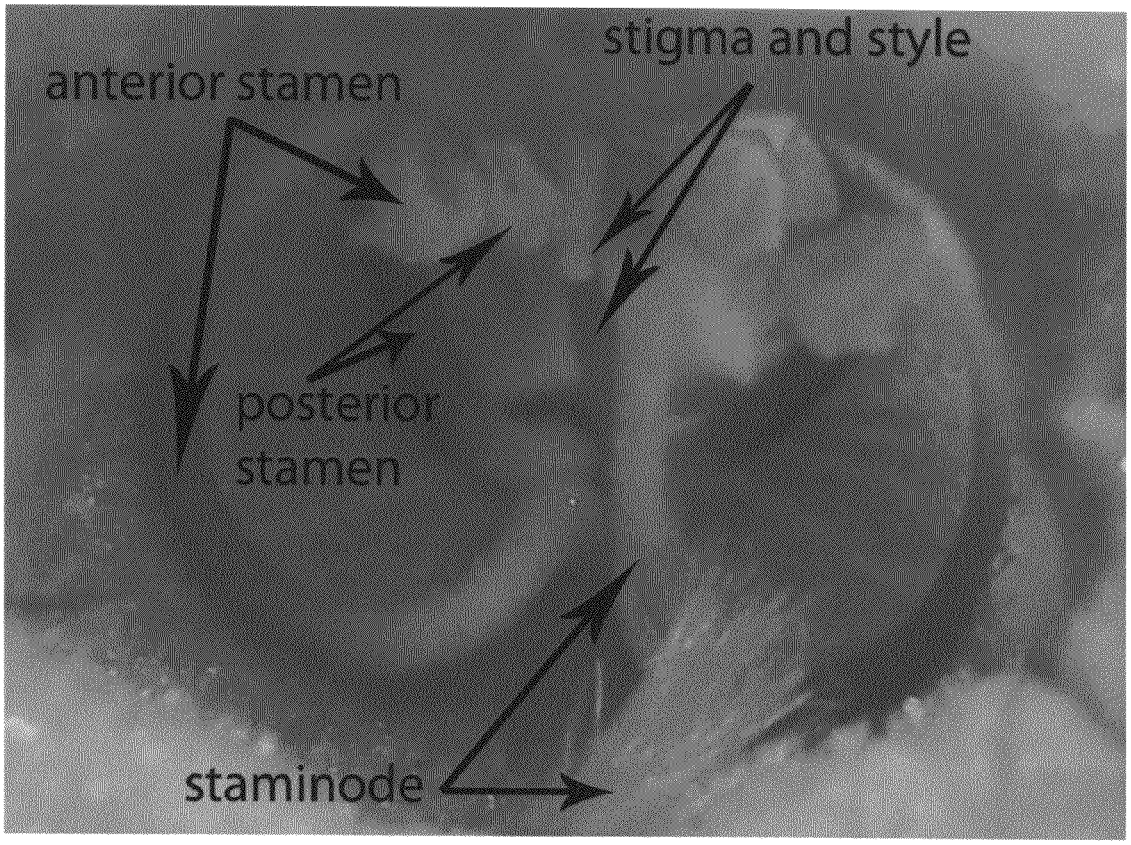
FIG. 12 is a macrophotograph of the structures of the throat/tube of a flower, seen in face view, of 'Red Headed Beauty' growing near Tucson, Ariz. Photo was taken May 2, 2010.
Figure 13:
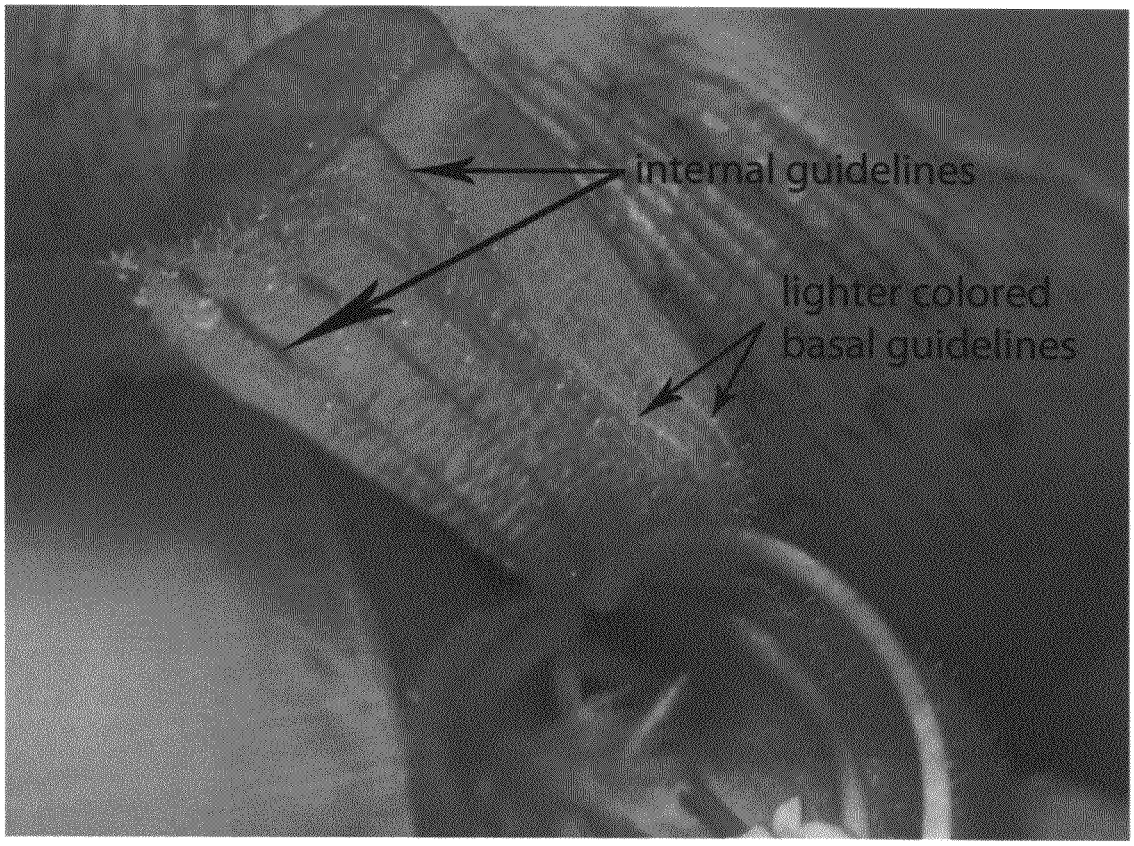
FIG. 13 is a macrophotograph of the inside tube of a dissected flower of 'Red Headed Beauty' original plant growing near Tucson, Ariz., showing internal guidelines. Photograph was taken Apr. 21, 2010.
Figure 14:
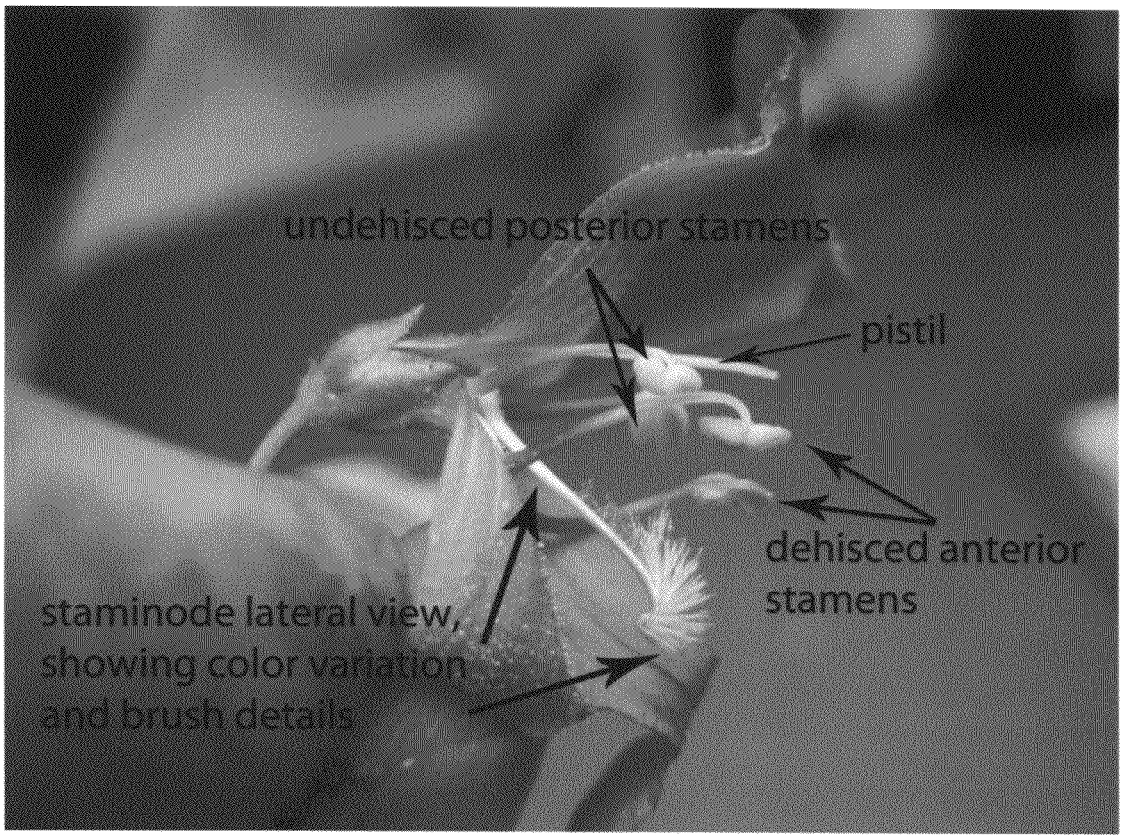
FIG. 14 is a macrophotograph of a dissected flower of 'Red Headed Beauty', illustrating internal structures and colors. Photo was taken Apr. 21, 2010.
Figure 15:
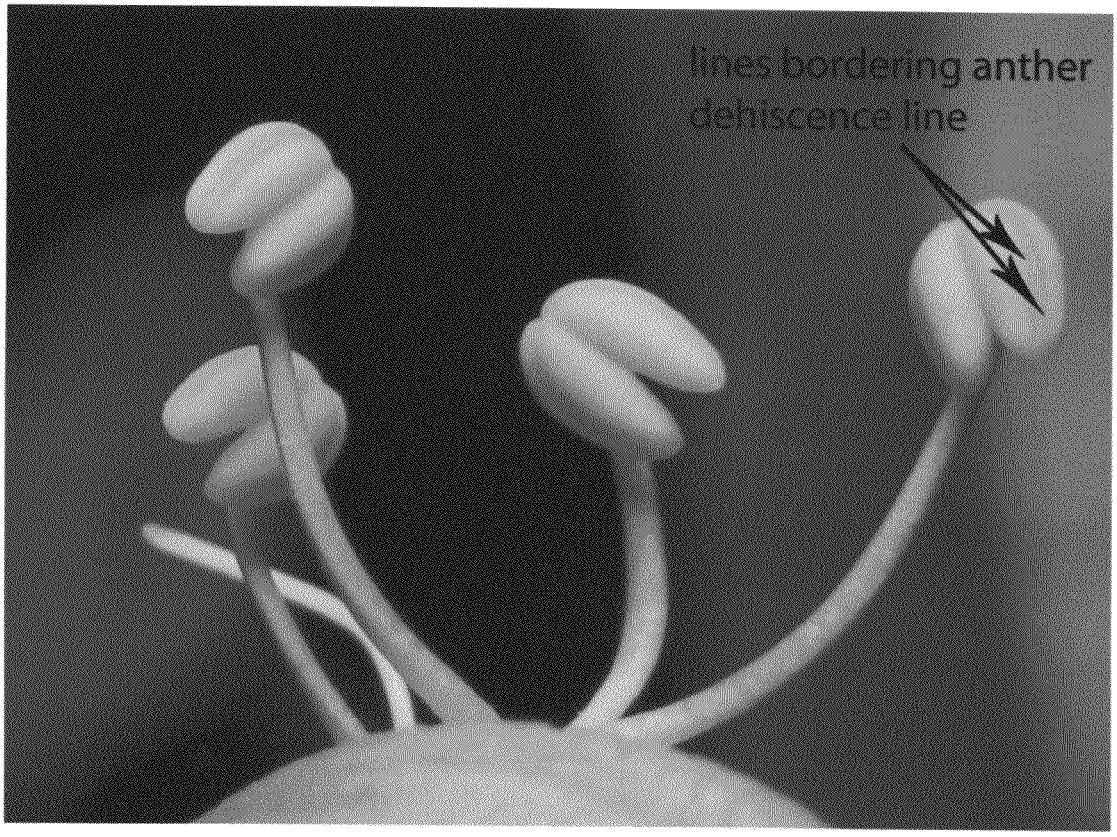
FIG. 15 is a macrophotograph of a dissected flower of 'Red Headed Beauty' original plant growing near Tucson, Ariz., illustrating typical appearance and colors of undehisced stamens with anther lines described elsewhere in the application.
Figure 16:
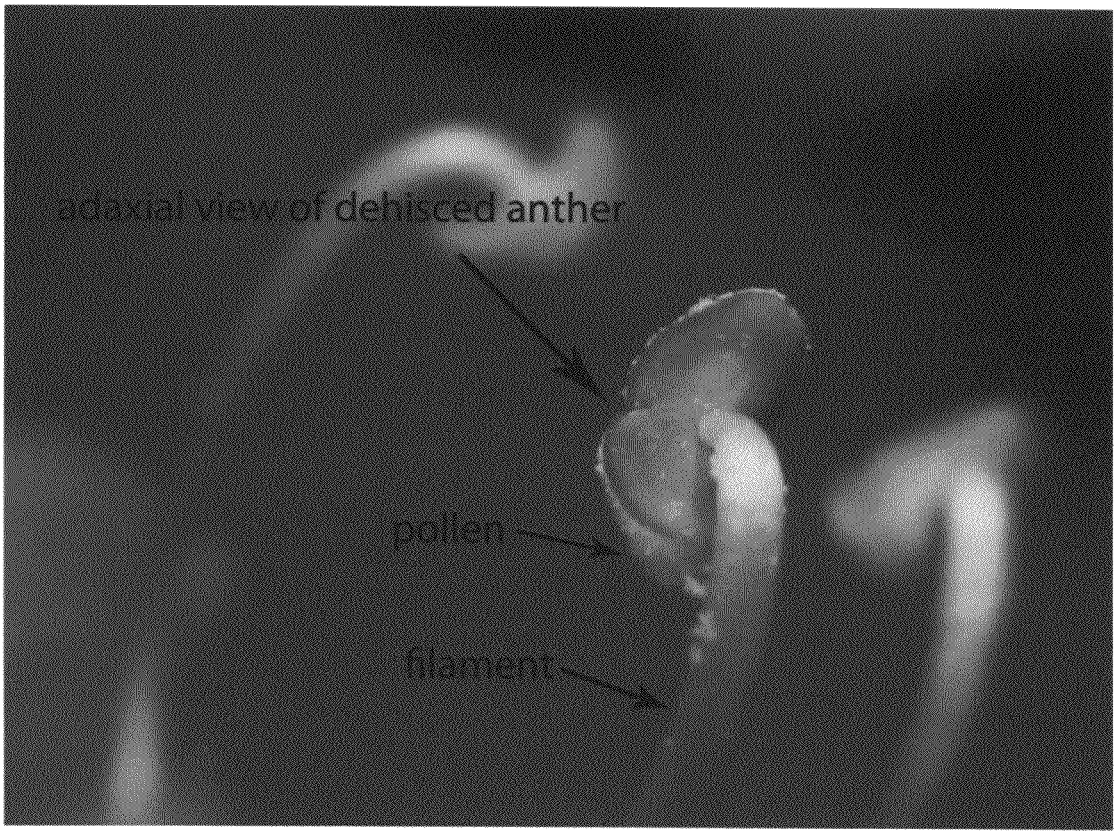
FIG. 16 is a macrophotograph of a dissected flower of 'Red Headed Beauty' original plant growing near Tucson, Ariz., illustrating the adaxial side of a dehisced stamen, structures and colors. Photo was taken Apr. 30, 2010.
Figure 17:
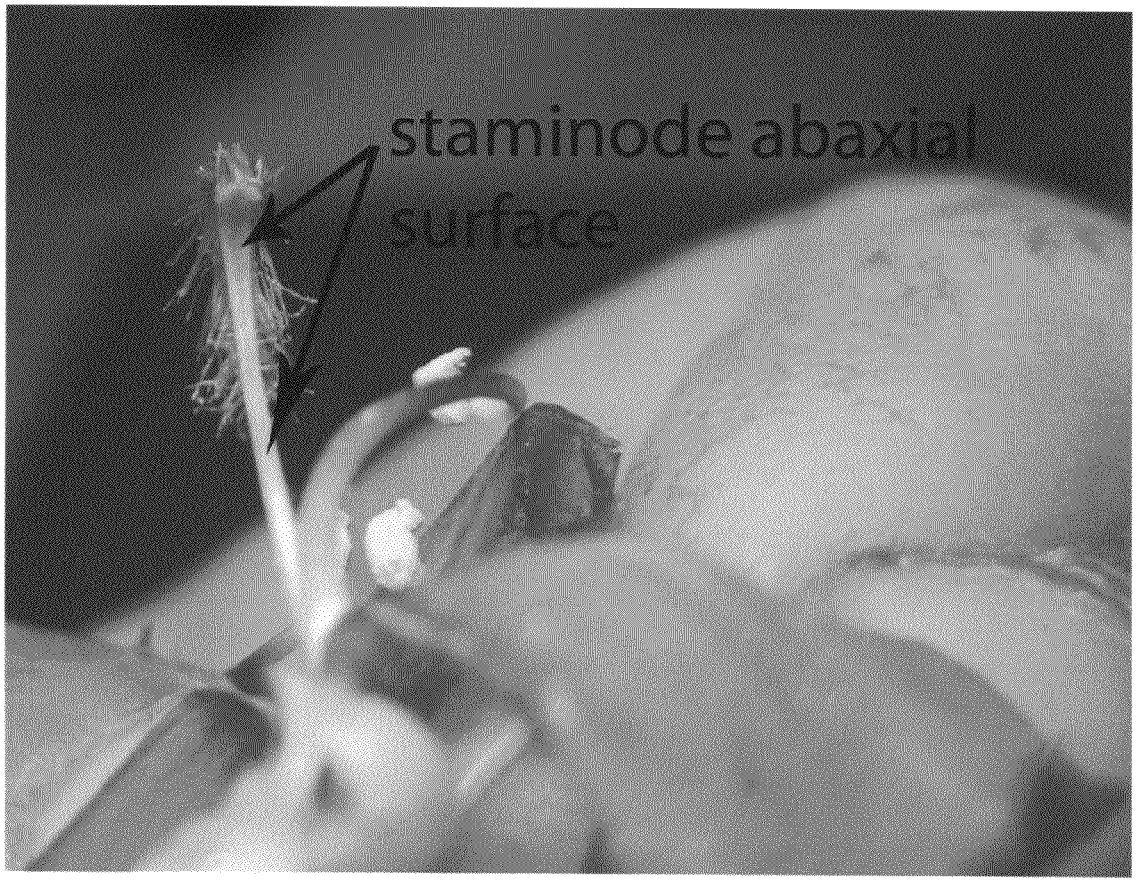
FIG. 17 is a macrophotograph of a dissected flower of 'Red Headed Beauty' original plant growing near Tucson, Ariz., illustrating the abaxial side of a staminode. Note the expanded, abaxially rolled tip and brush hairs. Photo was taken Apr. 17, 2010.
Figure 18:
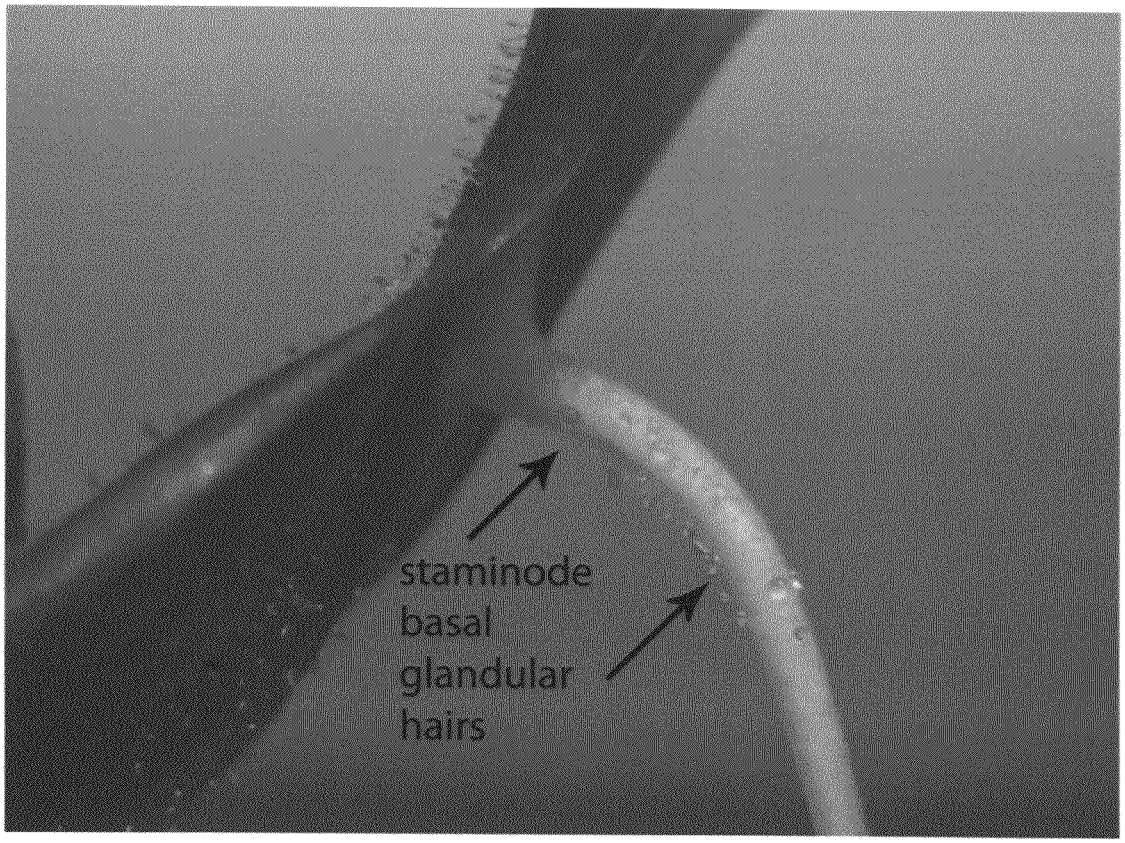
FIG. 18 is a macrophotograph of a dissected flower of 'Red Headed Beauty' original plant growing near Tucson, Ariz., illustrating the basal portion of the staminode, glandular hairs and attachment to the floral tube. Photo was taken Apr. 22, 2010.
Figure 19:
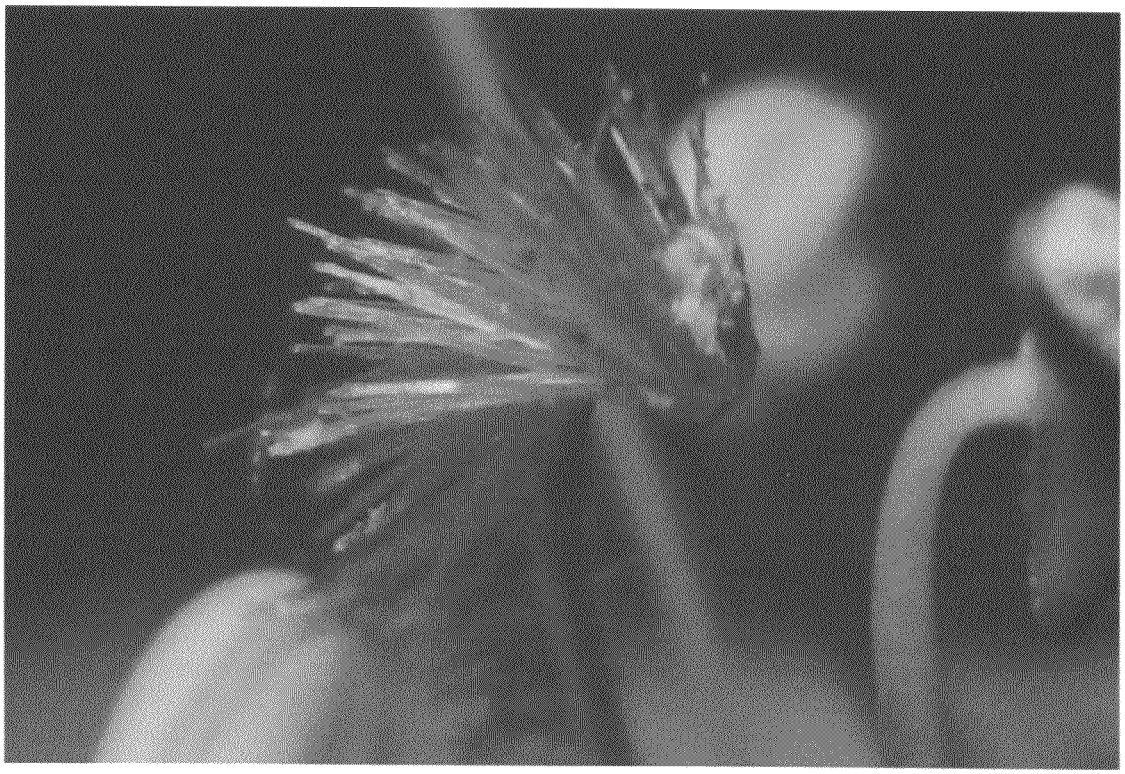
FIG. 19 is a macrophotograph of a dissected flower of 'Red Headed Beauty' original plant growing near Tucson, Ariz., illustrating the tip of a staminode, showing the mix of colored brush hairs present. Photo was taken Apr. 21, 2010.
Figure 20:
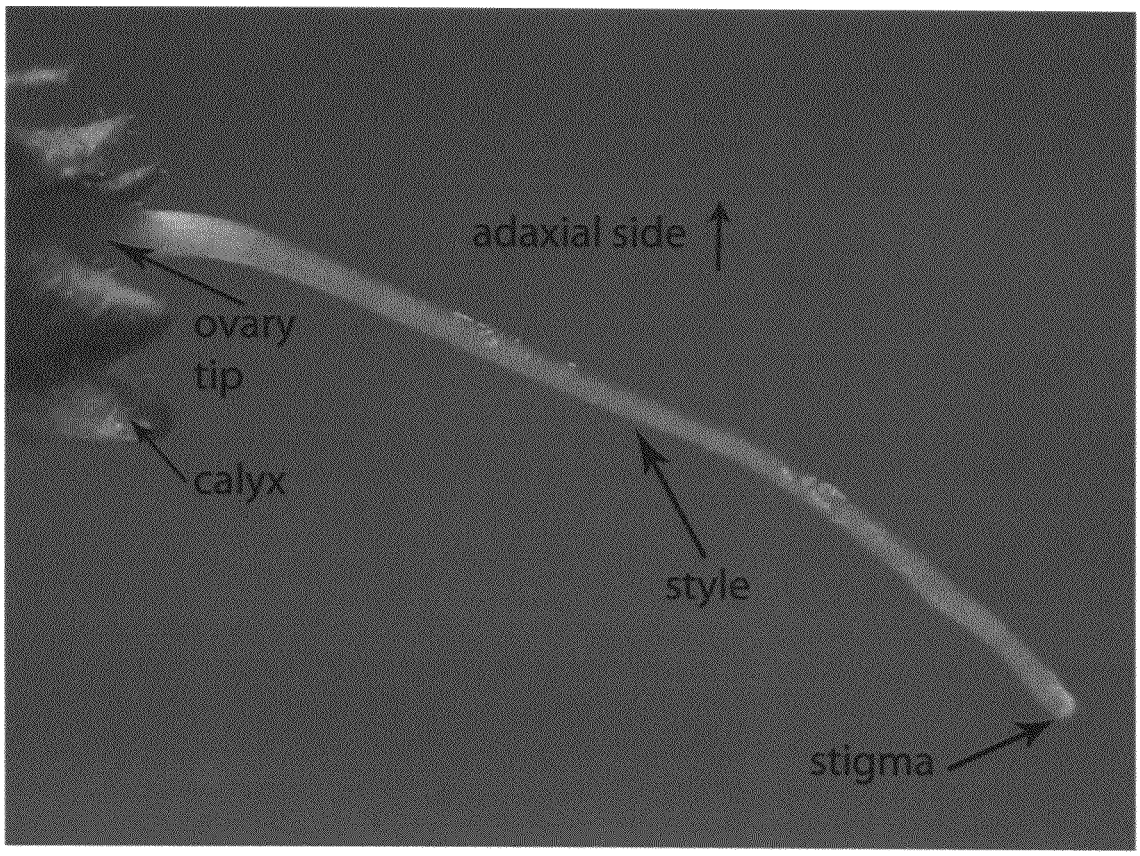
FIG. 20 is a macrophotograph of a dissected flower of 'Red Headed Beauty' original plant growing near Tucson, Ariz., illustrating the upper calyx and visible structures and colors of the pistil. Photo was taken Apr. 30, 2010.
Figure 21:
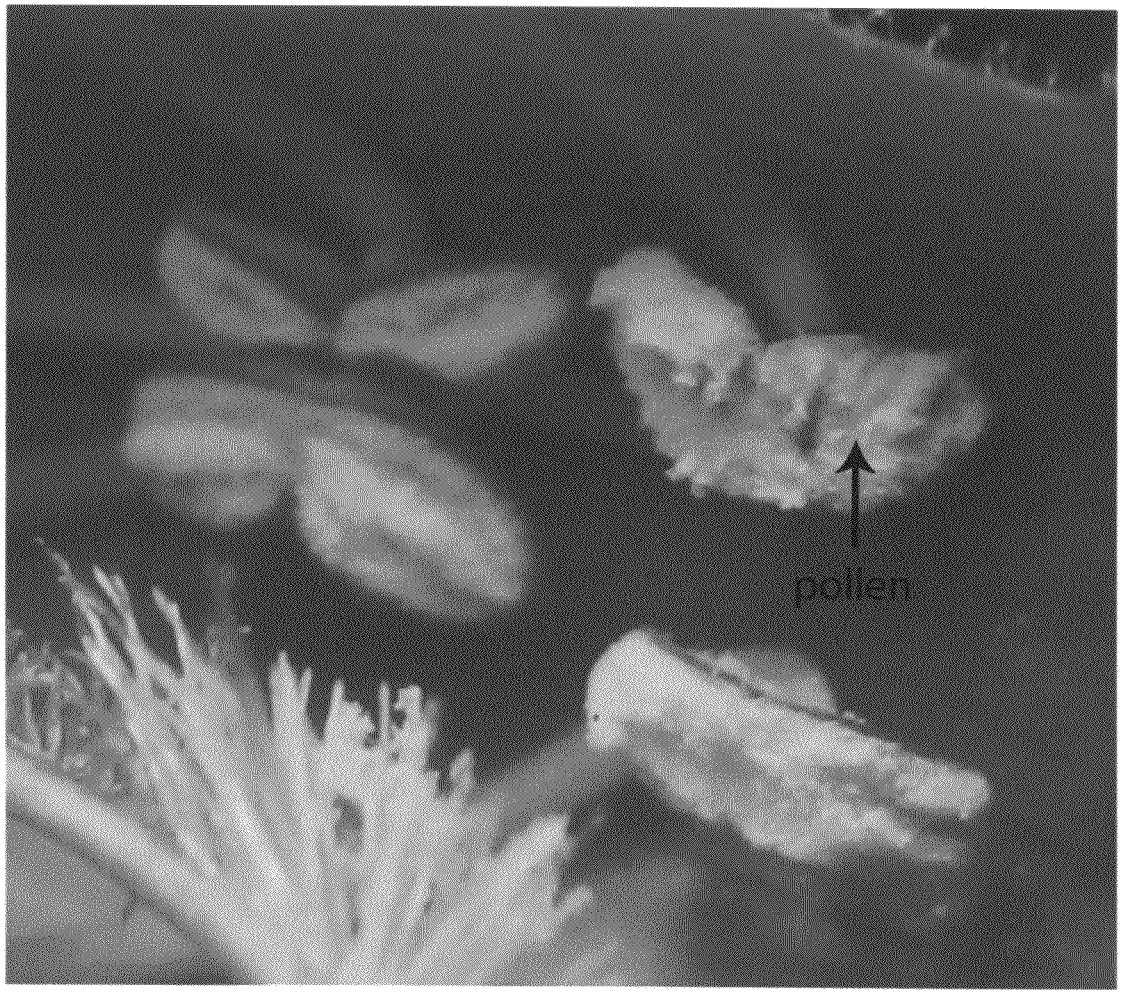
FIG. 21 is a macrophotograph of a dissected flower of 'Red Headed Beauty' original plant growing near Tucson, Ariz., illustrating the structures and colors of the abaxial side of dehisced stamens. Photo was taken Apr. 21, 2010.
Figure 22:
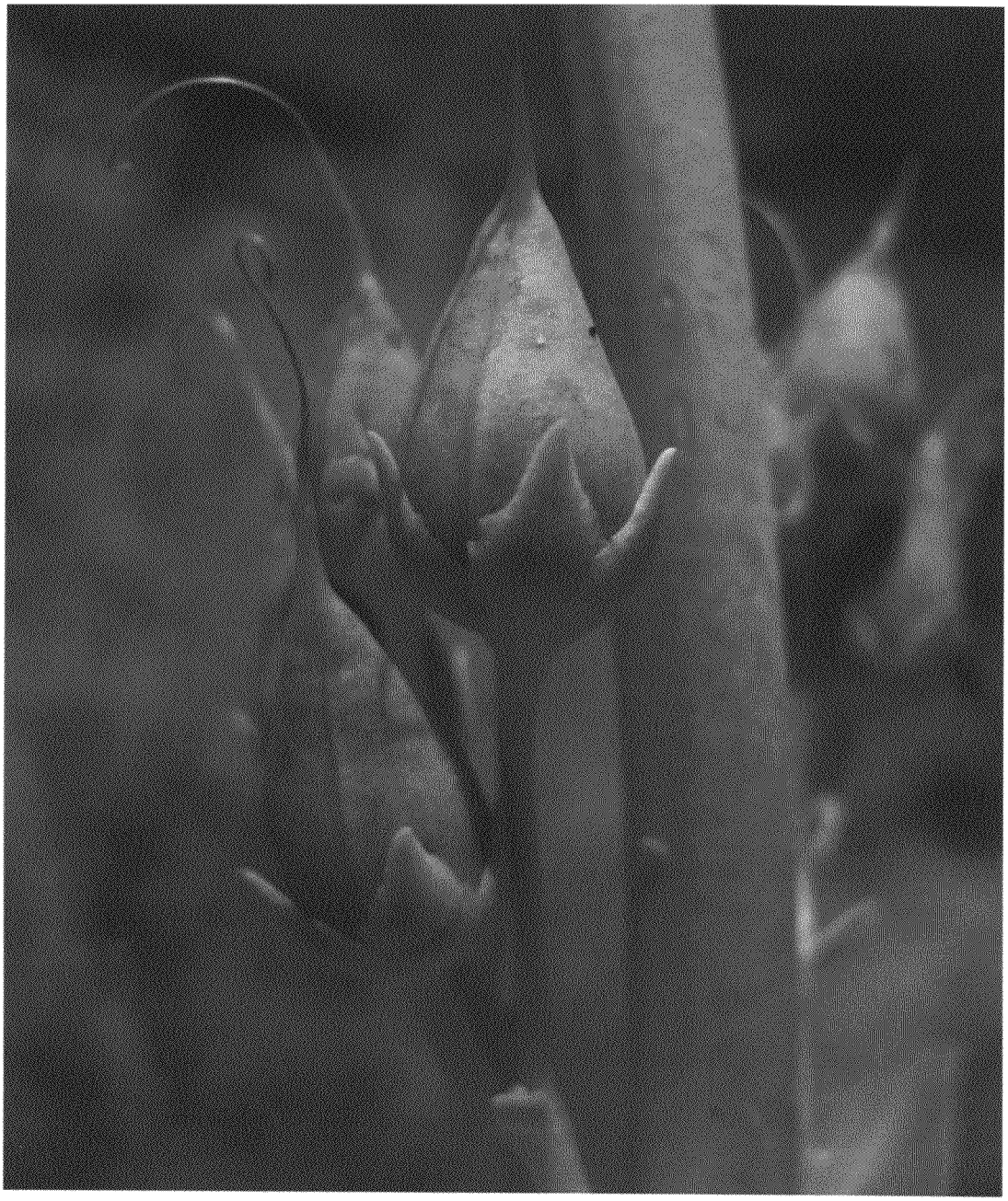
FIG. 22 is a macrophotograph of mature fruits of 'Red Headed Beauty' original plant growing near Tucson, Ariz. Photo was taken Jun. 10, 2010.
Figure 23:
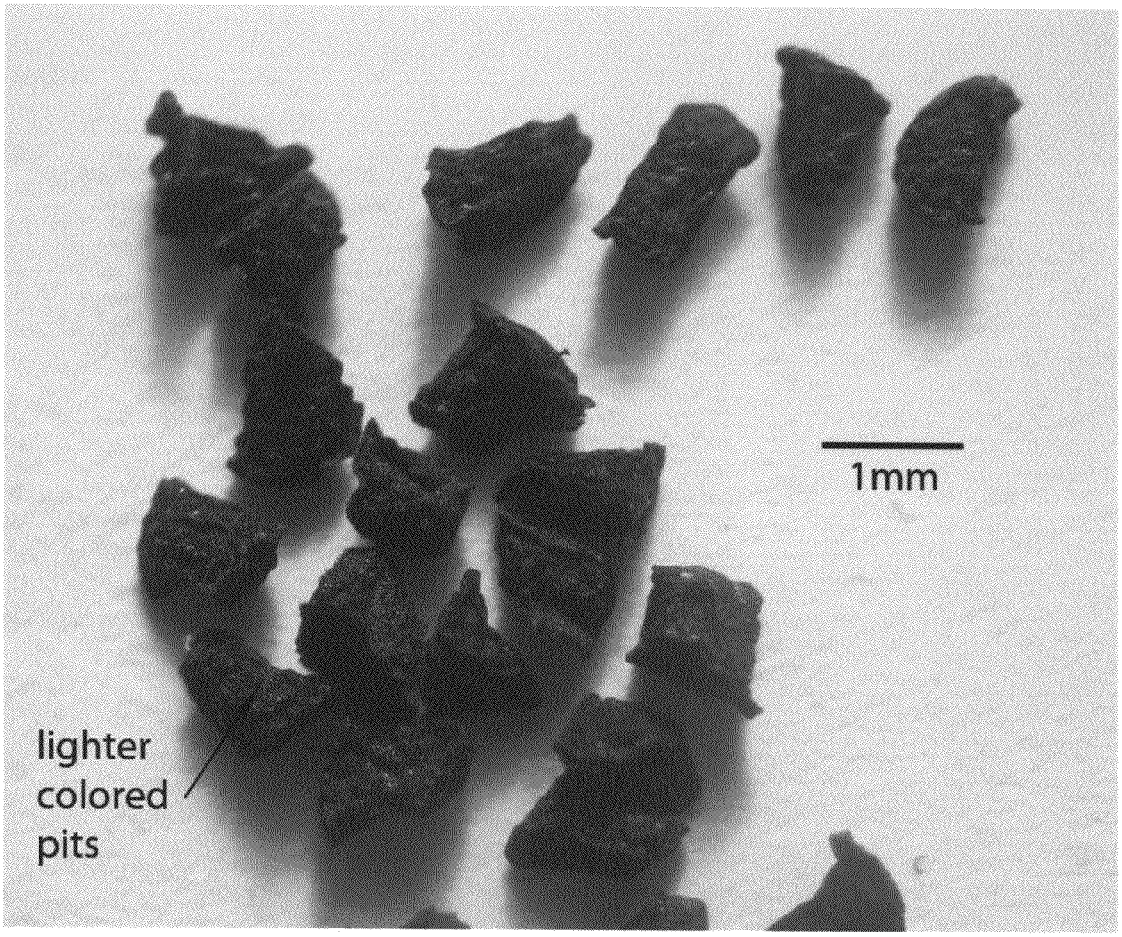
FIG. 23 is a photomicrograph of seeds of 'Red Headed Beauty' illustrating size, form and structures.

The following is a detailed description of the new *Penstemon* hybrid plant based upon measurements of two, three and five year old plants growing near Tucson, Ariz. The color descriptions are all based upon the Munsell Book of Color, Glossy Edition. Color names are as listed in *COLOR Universal Language and Dictionary of Names,* by Kenneth L. Kelly and Deane B. Judd; National Bureau of Standards special publication 440. Washington, D.C.: U.S. Department of Commerce, National Bureau of Standards, December 1976.

Plant name: 'Red Headed Beauty'.

Species or hybrid: *Penstemon* (*palmeri*×*parryi*)×*superbus.*

Original source plants: *P. palmeri:* cultivated plantings, *P. parryi:* cultivated plantings, *P. superbus:* cultivated plantings.

Original collection data (if known): *P. superbus* plantings were grown from seeds collected in a canyon habitat north of Hayden, Ariz. along AZ highway 77.

Mature plant size: Height 2-5 ft., width 2-5 ft., stems: upright to ascending. At age 5, the original pre-blooming plant is a suffrutescent mound 1 foot tall and 3 feet wide.

Stem color: Moderate yellow green, 7.5GY7/6, stem pubescence: none, stem surface: glaucous.

Stem diameter: 5-12 mm, stem length: 2-5 ft., flowering portion length: ⅓ to ⅗ of stem length.

Cauline leaf details:

*Cauline (stem) leaves.*—Type; simple.

*Cauline leaf venation.*—Pinnate, leaf arrangement: opposite.

*Cauline leaf margin.*—Entire with scattered obscure teeth, texture: leathery.

*Largest cauline leaf length.*—9-11 cm, width: 4-5 cm, leaf shape: lance ovate.

*Cauline leaf attachment.*—Clasping, sub-connate.

*Adaxial cauline leaf color.*—Moderate yellow green, 7.5GY5/5, leaf pubescence: none.

*Abaxial cauline leaf color.*—Moderate yellow green, 7.5GY5/5, leaf pubescence: none.

*Cauline leaf surface.*—Glaucous, notes: Thick leaves typical of Section *Peltanthera.* Leaf margins entire to obscurely toothed. Leaves tend to curve laterally abaxially.

*Cauline leaf note.*—During rapid growth of the flowering stalk, the new growth (leaves and stem tips) will temporarily exhibit bronzing.

Basal leaf details:

*Basal leaves.*—Length: 4.2-16 cm, width: 1.4-4.5 cm, basal leaf shape: oblanceolate, petiolate.

*Adaxial basal leaf color.*—Moderate yellow green, 7.5GY5/5, basal leaf pubescence: none.

*Abaxial basal leaf color.*—Moderate yellow green, 7.5GY5/5, basal leaf pubescence: none.

*Basal leaf surface.*—Glaucous, notes: Thick leaves typical of *Penstemon* Section *Peltanthera,* margins entire to obscurely toothed.

*Basal leaf note.*—During rapid growth, basal leaves will temporarily exhibit bronzing.

Bloom period: Late March through May in the Tucson, Ariz. area.

Inflorescence details:

*Inflorescence.*—Type: interrupted/verticillate subsecund thyrse with nodding (hooked) tips.

*Inflorescence height.*—2-5 ft., width of flower clusters: 5-7 cm.

*Flowers/verticillaster.*—4-18, verticillasters/inflorescence: 7-28.

*Flower number/inflorescence.*—49-280.

*Number of inflorescences/plant.*—1-30, depending upon age and growth conditions.

*Inflorescence note.*—Inflorescence is reminiscent of *P. superbus* in form, but with much larger flowers of a different color.

*Primary bracts.*—Shape: acuminate, length: 5-30 mm, width: 2-28 mm, color: moderate yellow green, 7.5GY5/5. Note: few to no glandular hairs, similar to cauline leaves except for shape and size.

*Primary pedicels.*—Length: 10-14 mm, width: 1 mm, color: varies from dark purplish red, 10RP3/6 to moderate yellow green, 7.5GY7/6. Note: few glandular hairs present, mostly concentrated near the calyx base.

*Secondary pedicels.*—Length: 5-10 mm, width: 1 mm, color: varies from dark purplish red, 10RP3/6 to moderate yellow green, 7.5GY7/6. Note: glandular hairs as in primary pedicels.

Flower details:

*Flowers.*—Length: 18-22 mm, throat diameter: 8-10 mm, face diameter: 22-28 mm.

*Corolla shape.*—Ventricose/ampliate.

*Corolla face shape.*—Bilabiate, nearly rotate, upper lip reflexed, lower lip somewhat extended, corolla lobes rounded.

*Floral aroma.*—Slight, smells faintly like *P. palmeri.*

*Floral glandular hairs.*—Outside tube: dense, face: medium, inside tube: medium-scattered, calyx: medium, pedicel: few, mostly near the calyx base.

*Corolla details.*—Exterior tube color: deep purplish red, 10RP3/10, face color: vivid purplish red, 7.5RP3/16 fading to deep purplish red, 7.5RP3/12.

*Interior of corolla tube color.*—Moderate purplish red, 5RP4/10.

*Guidelines.*—Obscure; color and type: very dark red, 2.5R1/6. Centered on each petal, lines extend from about midway into the petals to nearly the interior base of the corolla. Fainter, shorter parallel lines lie between the primaries within the corolla tube. Additional, parallel lighter lines may be seen near the interior tube base.

*Staminode.*—Included; staminode shape: sigmoid.

*Staminode length* (*straight measurement, not uncoiled, from tube attachment point*).—13.5 mm.

*Staminode filament diameter.*—0.5-0.75 mm.

*Staminode tip.*—Dialated, abaxially rolled, and adaxially bearded.

*Staminode beard/brush.*—One sided adaxially on upper ⅗ of staminode.

*Staminode brush details.*—3 types: basal ⅓ of beard hairs 0.7 mm long, distal ⅔ of beard hairs 1.5 mm long.

*Staminode brush hair color*(*s*).—Basal ⅓: strong yellow, 2.5Y7/10, middle ⅓: moderate yellow, 5Y7/6, distal ⅓: mixed hair colors as follows: ¼ of hairs deep purplish red, 10RP3/10, ¾ of hairs dark orange yellow, 7YR6/8.

*Staminode filament.*—Abaxial surface more deeply colored. Color intensity appears to vary with growth conditions.

*Staminode filament color*(*s*).—Abaxial side: distal ⅗: deep purplish red, 5RP3/12 or lighter, depending upon growth conditions, basal ⅖: light yellow green, 2.5GY9/6; adaxial side: basal ⅓: light yellow green, 2.5GY9/6, middle below brush: pale pink, 2.5R9/2.

*Staminode notes.*—Staminode is sigmoid with the tip recurved abaxially 180 degrees. Glandular hairs are present basally especially on the adaxial side.

*Stamens.*—4 fertile, type: peltate-explanate, filament length (straight measurement, not uncoiled).

*Distal stamens.*—14 mm; basal stamens: 12 mm, filament diameter (both types): 0.5 mm.

Anther details:

*Undehisced anther; size* (*length×width×thickness*).—Distal stamens: 3×2.5×1.1 mm, basal stamens: 3×2.3×1.1 mm.

*Undehisced anther colors and description.*—Exterior side (filament attachment side): variable in color, very pale purple, 7.5P9/4 or whiter. Two parallel lines lie on either side of the dehiscence line, color: vivid purple, 7.5P5/14. Interior side color is similar to exterior side.

*Dehisced anther; size* (*length×width*).—2.5×1 mm.

*Dehisced anther exterior color and description.*—Margin: very dark purple, 7.5P1/6 grading to between light and moderate orange yellow, 10YR8/8 at the anther attachment point.

Pollen color: Pale greenish yellow, 7.5Y9/4.

Stamen filament details: 3 color zones as listed below, clear secretions from glandular hairs are present at the basal color transition zone and sometimes just below it.

*Stamen filament color*(*s*).—Basal ¼: pale greenish yellow, 10Y9/4; middle ½: strong purplish red, 6RP4/12; distal ¼: whiter than light pink, 2.5R9/4.

Pistil length: 20-23 mm.

Style:

*Size* (*length×diameter*).—14×0.25-0.33 mm.

*Shape.*—Curved abaxially.

*Style color*(*s*).—Near tip: light reddish purple, 2.5RP6/8 or whiter, near base: deep reddish purple, 2.5RP3/12 or whiter.

*Style notes.*—Style curves abaxially near the tip, more as the flower ages. There is considerable variation in style color from flower to flower.

Calyx details:

*Length.*—6-9 mm.

*Width.*—4-5 mm.

*Calyx lobes.*—Ovate, margins of calyx lobes hyaline.

*Calyx color.*—Varies from deep brown, 2.5YR2/7 to deep yellow green, 4GY4/8 depending upon growing conditions.

Plant fertility: High (near normal). Notes: Plants are self and probably cross fertile, at least with closely related species.

Fruit:

*Type.*—2 celled septicidal/loculocidal capsule dehiscing on 4 lines.

*Fruit shape.*—Ovoid/attenuate, ellipsoidal in cross section.

*Fruit size* (*length×width×thickness*).—L: 11-14 mm, W: 6-8 mm, T: 5.5-7 mm.

*Fruit color.*—Light yellow green, 4GY8/5 near maturity; moderate brown, 7.5YR3/5 when ripe and dry.

Seeds/fruit: 30-50. Note: Thickness is the measurement at the widest point of the fruit perpendicular to the septum.

Seeds:

*Size.*—1 mm long.

*Color.*—Reddish black, 10R1/1.

*Viability.*—High.

*Shape.*—Variable and irregular, angular, rugose, evenly marked with lighter colored pits visible under 20× magnification.

COMPARISONS TO RELATED *PENSTEMON*

Compared to its three parents (*Penstemon palmeri, P. parryi* and *P. superbus*) 'Red Headed Beauty' displays greater vigor, overall size, bloom period and flower size. Of its parents, only *Penstemon superbus* has comparable longevity to 'Red Headed Beauty'.

*Penstemon* hybrid 'Red Headed Beauty' may be distinguished from its parents as follows:

*Penstemon superbus* and *Penstemon parryi* both have entire leaf margins, while *Penstemon* hybrid 'Red Headed Beauty' has scattered obscure teeth on some of its leaves. *Penstemon palmeri* may be contrasted by its sharply toothed leaf margins.

*Penstemon parryi* and *Penstemon palmeri* are generally short lived under Tucson conditions, with a lifespan of 1-3 years. *Penstemon superbus* is longer lived, with some plants lasting for up to 10 years. *Penstemon* hybrid 'Red Headed Beauty' shows no signs of declining vigor at age 5, and appears to be potentially quite long lived.

*Penstemon parryi* has a corolla diameter of 13-17 mm, tube opening of 5-8 mm and tube length of 15-18 mm. Flowers vary in color from an occasional white (lighter than 2.5GY9/6) or deep yellowish pink (5R6/12) to strong purplish red (10RP9/6). The tube of the flowers is generally darker with guidelines extending into the petals. The face of the corolla of *Penstemon parryi* is covered with glandular hairs at a moderate density. The flowers are somewhat bilabiate. The inflorescence is paniculate.

*Penstemon superbus* has a corolla diameter of 15-19 mm, tube opening of 4-6 mm and tube length of 15-20 mm. Flowers vary in color from strong red (2.5R4/12) to vivid red (7.5R4/20). The tube of the flowers is generally similar in color to or lighter than the corolla with obscure guidelines. The face of the corolla is densely covered with glandular hairs. The flowers are nearly rotate. The inflorescence is verticillate.

*Penstemon palmeri* has a corolla diameter of 20-25 mm, tube opening of 15-20 mm and a tube length of 25-30 mm. Flowers vary from light purplish pink (10P9/6) to nearly pure white. The tube of the flowers is generally lighter than the corolla, with guidelines extending into the lower 3 petals only. The face of the corolla lacks glandular hairs. The tube is greatly inflated and flowers are strongly bilabiate. The flowers produce a strong, sweet fragrance. The inflorescence is interrupted, but appearing continuous and subsecund.

*Penstemon* hybrid 'Red Headed Beauty' has a corolla diameter of 22-28 mm, a tube opening of 8-10 mm and a tube length of 18-22 mm. Flowers vary in color from vivid purplish red (7.5RP3/16) to deep purplish red (7.5RP3/12). The face of the corolla is covered with glandular hairs at a medium density. The tube is ventricose ampliate. The corolla is bilabiate, nearly rotate, with the upper lip reflexed and the lower lip somewhat extended. The corolla tube is slightly lighter than the corolla, with obscure guidelines. The flowers have a slight fragrance, but similar to that of *Penstemon palmeri*. The inflorescence is an interrupted/verticillate subsecund thyrse.

*Penstemon* hybrid 'Red Headed Beauty' is partially related to the *Penstemon* 'Mexicali' group of hybrids, sharing *Penstemon palmeri* and *Penstemon parryi* as parents, but differing in that *Penstemon* hybrid 'Red Headed Beauty' has *Penstemon superbus* as a pollen parent, while the 'Mexicali' hybrids have a *Penstemon* hybrid of the *Penstemon* section *Fasciculatus* as one of their parents. The plants of *Penstemon* hybrid 'Red Headed Beauty' may be distinguished from the 'Mexicali' hybrids by the leaves, which in the case of 'Red Headed Beauty' are leathery and moderate yellow green (7.5GY5/5) colored, while the 'Mexicali' hybrids are not leathery, have adaxial leaf surfaces colored strong olive green (5GY3/8) to dark olive green (7.5GY2/4). 'Mexicali' hybrids are sprawling and bushy with lance/linear, serrate leaves, while 'Red Headed Beauty' grows basally with long up reaching flower stalks and has larger, lance ovate cauline leaves that are mostly entire with scattered, obscure teeth.

I claim:

1. A new and distinct *Penstemon* hybrid plant substantially as described and illustrated herein.

* * * * *